United States Patent
Ryan et al.

(10) Patent No.: US 7,148,022 B2
(45) Date of Patent: Dec. 12, 2006

(54) ASSAY FOR ANTI-VIRAL AGENT

(75) Inventors: Michael Ryan, North Haugh (GB); Tom Wileman, Woking (GB); Caroline Knox, North Haugh (GB)

(73) Assignee: The University Court of the University of St. Andrews, St Andrews (GB)

( * ) Notice: Subject to any disclaimer, the term of this patent is extended or adjusted under 35 U.S.C. 154(b) by 94 days.

(21) Appl. No.: 10/450,342

(22) PCT Filed: Dec. 12, 2001

(86) PCT No.: PCT/GB01/05487

§ 371 (c)(1),
(2), (4) Date: Nov. 6, 2003

(87) PCT Pub. No.: WO02/48708

PCT Pub. Date: Jun. 20, 2002

(65) Prior Publication Data

US 2005/0260559 A1 Nov. 24, 2005

(30) Foreign Application Priority Data

Dec. 12, 2000 (GB) .................... 0030203.4

(51) Int. Cl.
*C12Q 1/00* (2006.01)
*C12Q 1/70* (2006.01)
*G01N 33/53* (2006.01)
*C07K 4/00* (2006.01)
*C07K 14/00* (2006.01)

(52) U.S. Cl. ............... 435/7.1; 435/4; 435/5; 435/7.2; 435/7.9; 503/300; 503/350

(58) Field of Classification Search ............... 435/4, 435/5, 7.1, 7.2, 7.9, 7.93, 235.1; 530/300, 530/350

See application file for complete search history.

(56) References Cited

FOREIGN PATENT DOCUMENTS

WO   WO 99/29908   6/1999

OTHER PUBLICATIONS

GenePept NP_937964, 2C [Foot-and-mouth disease virus Asia 1], NCBI printout.*
Argos et al., Nucleic Acids Research, vol. 12 No. 8, pp. 7251-7267 (Sep. 1984).*
Pfister et al., Journal of Biological Chemistry, vol. 274 No. 11, pp. 6992-7001 (Mar. 1999).*
Echeverri et al., Virology, vol. 208 No. 2, pp. 540-553 (Apr. 1995).*
Gazina et al., Journal of Virology, vol. 76 No. 21, pp. 11113-11122 (Nov. 2002).*
Weissenhorn et al., Nature, vol. 387 No. 6631, pp. 426-430 (May 1997).*

* cited by examiner

*Primary Examiner*—Bruce R. Campell
*Assistant Examiner*—Zachariah Lucas
(74) *Attorney, Agent, or Firm*—Drinker Biddle & ReathLLP; Daniel A. Monaco

(57) ABSTRACT

There is provided an assay for selecting an anti-viral agent effective against picornavirus infection. The assay selects an agent which disrupts the association between picornavirus protein 2C and the host cell protein D-AKAP2, which association has been found to be essential for successful viral replication. Also disclosed are anti-viral agents having such properties and a method of combating picornavirus replication.

6 Claims, 2 Drawing Sheets

SEQUENCE LISTING

```
<160> NUMBER OF SEQ ID NOS: 7

<210> SEQ ID NO 1
<211> LENGTH: 32
<212> TYPE: DNA
<213> ORGANISM: Artificial
<220> FEATURE:
<223> OTHER INFORMATION: PCR primer (forward) for D-AKAP2

<400> SEQUENCE: 1
aaaggatcca aagggtccat gttctcacaa gc                                32

<210> SEQ ID NO 2
<211> LENGTH: 31
<212> TYPE: DNA
<213> ORGANISM: Artificial
<220> FEATURE:
<223> OTHER INFORMATION: PCR primer (reverse) for D-AKAP2
```

-continued

```
<400> SEQUENCE: 2
aaagaattct cacagcttgg cagaggtctc c                                   31

<210> SEQ ID NO 3
<211> LENGTH: 33
<212> TYPE: DNA
<213> ORGANISM: Artificial
<220> FEATURE:
<223> OTHER INFORMATION: PCR primer (forward) for plasmid pMR15

<400> SEQUENCE: 3
gatatcggat ccatgctcaa agcacgtgac atc                                 33

<210> SEQ ID NO 4
<211> LENGTH: 39
<212> TYPE: DNA
<213> ORGANISM: Artificial
<220> FEATURE:
<223> OTHER INFORMATION: PCR primer (reverse) for plasmid pMR15

<400> SEQUENCE: 4
gtttgcaagg aagctgccgc cctggccctg gccagattt                           39

<210> SEQ ID NO 5
<211> LENGTH: 33
<212> TYPE: DNA
<213> ORGANISM: Artificial
<220> FEATURE:
<223> OTHER INFORMATION: PCR primer (forward) for plasmid pMR15

<400> SEQUENCE: 5
aaatctggcc agggcggcag cttccttgca aac                                 33

<210> SEQ ID NO 6
<211> LENGTH: 33
<212> TYPE: DNA
<213> ORGANISM: Artificial
<220> FEATURE:
<223> OTHER INFORMATION: PCR primer (reverse) for plasmid pMR15

<400> SEQUENCE: 6
gatatcgaat tctcactgct tgaagatcgg gtg                                 33

<210> SEQ ID NO 7
<211> LENGTH: 89
<212> TYPE: RNA
<213> ORGANISM: Picornavirus

<400> SEQUENCE: 7
auaaaacagg cguacaaggg uaccgcaaua ccggaguacu agccgccacg ugggccucug     60
gggcgggugc aaccccagag cuguuuuaa                                      89
```

ASSAY FOR ANTI-VIRAL AGENT

The present invention relates to an assay for an anti-viral agent for picornaviruses.

BACKGROUND OF THE INVENTION

Picornaviruses are single positive strand RNA viruses. The genome of approximately 7,500–8,250 bases contains a single long open reading frame encoding a large polyprotein, usually approximately 230 kDa. The polyprotein is processed auto-proteolytically by virus-encoded proteases. The 'primary' cleavages separate the polyprotein into the structural capsid protein (P1), and non-structural proteins involved in virus replication (P2 and P3), see FIG. 1. All three primary proteins (P1, P2 and P3) undergo post-translational cleavage to produce mature proteins (reviewed in reference [1]).

In the case of the rhino- and enteroviruses this processing is achieved by the 2A proteinase cleaving at its own N-terminus, whilst in the aphtho- and cardioviruses the 2A protein mediates cleavage at its own C-terminus[1]. In the latter viruses this cleavage is mediated by an oligopeptidic tract (18 amino acids) corresponding to the complete 2A protein of Foot-and-Mouth Disease Virus (FMDV), or, just the C-terminal region of the larger (~145 amino acids) cardiovirus 2A protein[2]. The sequence is able to mediate cleavage in entirely foreign protein contexts[3] and has been used in a wide range of co-expression studies[4-6]. The corresponding primary cleavage in the hepato- and parechoviruses is mediated by the 3C proteinase (see FIG. 1).

It is known that large numbers of membrane vesicles are produced in the cytoplasm of picornavirus-infected cells[7]. These vesicles are thought to arise from the transitional smooth areas of the Endoplasmic Reticulum (ER) that produce transport vesicles which move proteins from the ER to the Golgi[8]. It is also known that Brefeldin-A, a drug that blocks the formation of ER-derived transport vesicles, is one of the most potent known inhibitors of picornavirus replication[9,10] and that normal membrane transport from the ER to the Golgi is blocked in picornavirus infected cells[11,12]. Picornavirus infection appears, therefore to change the balance of membrane budding and fusion which is normally maintained between the ER and Golgi compartments. Transport vesicles leaving the ER do not appear to fuse with the Golgi, but are diverted from the secretory pathway to function at sites of virus replication, explaining why the Golgi is absent later in infection. Indeed, the loss of the Golgi is coincident with the formation of virus replication complexes in the cytoplasm. These appear as rosettes of large vesicles surrounding a compact central membrane system.

As early as 1982 Semler and co-workers demonstrated the association of the non-structural protein 3AB with membranes[13]. Other non-structural viral proteins 3AB, 2BC, 2B, 2C have since been shown to localise to crude membrane fractions[14], and to the ER[15]. The membrane association of 3A and 3AB has been explained by the presence of 20 hydrophobic amino acids at the C-terminus of 3A, and deletion of this region abrogates membrane binding. The membrane association of 2C and 2BC was proposed via an amphipathic helix that produces a hydrophobic patch at the N-terminus of 2C[12].

Importantly, protein 2C has been localised to electron-dense coats within the regions of ER membrane producing cytoplasmic vesicles, and within membrane vesicles of the replication complex[14]. The observation that 3A, 3AB, 2BC and 2B bind membranes makes them strong candidates as inhibitors of membrane traffic in cells. Indeed recent studies show that 2BC and 2C induce the formation of vesicles[14], and 3A and 2B block secretion, when expressed alone in cells[11,12].

In picornaviruses, RNA replication is solely a function of the P2 and P3 regions of the polyprotein. A full-length negative sense copy of the genomic, positive sense, RNA is synthesised and acts as a template for the synthesis of full length positive RNA strands. In the case of the entero- and rhinoviruses 2A is a proteinase[1] and forms part of the P2 primary cleavage product. The function of protein 2B is unknown, protein 2C is discussed in detail below, protein 3A is thought to function as a 'donor' for the protein 3B (or VPg) which becomes covalently bound to the 5' terminus of both positive and negative strand RNA. Protein 3C is a proteinase (see reference [1]), which serves to mediate a primary cleavage between P2 and P3 and subsequently processes P2 and P3 ('secondary' cleavages).

Protein 2C is the second largest mature protein (approximately 37 kDa) and is the most highly conserved picornavirus protein. Indeed, homologues of 2C are found within other members of the picornavirus 'supergroup'—comprising both (non-picornavirus) animal viruses (caliciviruses, hepatitis E viruses; various insect viruses) and numerous plant viruses (comoviruses, nepoviruses).

Based on sequence alignments it was proposed that protein 2C contained NTP binding motifs[16] and could function as a helicase. Although it has not proved possible to demonstrate helicase activity this notion has been stated in the literature and is believed to be correct within the current understanding of picornavirus protein function[41-44].

Protein 2C is known to have ATPase/GTPase activity[17,18]. Membrane binding activity maps to the N-terminal region (amino acids 21–54) of poliovirus 2C, containing one of the putative amphipathic helices (See FIG. 2, panel A). Protein 2C is not glycoslyated nor cleaved by signal peptidases[19]. Expression of 2C induces membrane proliferation and blocks the exocytic pathway[20,21].

Furthermore, 2C is an RNA-binding protein with sites mapped to the N- and C-terminal regions (amino acids 21–45 and 312–319)[19], summarised in FIG. 2, panel A. The RNA sequences bound by 2C were determined to be a stem of a clover-leaf structure SEQ ID NO:7 (see FIG. 2, panel B) initially characterised in the positive RNA sense and predicted to be present in the negative sense (anti-genome) RNA. Interestingly, one can see that one component of the RNA-binding domain is contained within that determined for membrane binding.

The specificity of signalling molecules is greatly enhanced by their sub-cellular compartmentalisation within the cell. The distribution of these molecules is governed by their association with (membrane-bound) anchoring proteins which place these enzymes close to their appropriate effectors (reviewed in [20–22]). The dual-specificity kinase anchoring protein 2 (D-AKAP2) binds the regulatory subunits (both RI and RII) of protein kinase A (PKA). Originally identified by their co-purification with RII after cAMP-sepharose chromatography[23], AKAPs were further characterised using their property of binding RII immobilised to nitrocellulose or similar solid-phase supports[24]. D-AKAP2 sequences are available for mouse[25], human[26] and we have completely sequenced the porcine D-AKAP2 [27] identified by the yeast screen. In each case a putative 'regulator of G-protein signalling' (RGS) domain is present, although sequence similarities between D-AKAP2 and the RGS domains of other proteins is low. The binding of PKA regulatory subunits is thought to be mediated by an amphipathic helix[21]. Inspection of aligned D-AKAP2 sequences shows similarity between the C-terminus and RII binding sites determined for other AKAPs[21]. The PKA (RII)/D-AKAP2 binding is high (low nanomolar) affinity[28] but does require prior dimerisation of the RII subunit[19]. D-AKAP2 shows a wide tissue distribution although its location(s) at the sub-cellular level has not been determined.

It has now be found that a strong interaction exists between FMDV protein 2C and the cellular membrane protein D-AKAP2. When FMDV 2C is used as 'bait' in the 2-hybrid yeast screen, a strong interaction is observed with the C-terminal region (50 amino acids) of D-AKAP2. The results from our genetic screen have been confirmed by direct biochemical assays. D-AKAP2 binds protein kinase A (PKA) and has dual specificity for both the regulatory subunits (RI and RII) of this enzyme (see above). The yeast two-hybrid 2A:D-AKAP2 interaction was confirmed by direct biochemical binding assays using FMDV 2C translated in vitro and from infected-cell lysates. We extended these observations by the analysis of a site-directed mutagenetic form of 2C. A single mutation in the NTP-binding motif ($K^{116}$ to Q) renders this form of 2C unable to reorganise the membrane structure of transfected cells but does not alter the binding to D-AKAP2 in biochemical assays.

Since the membrane binding region of 2C has been mapped to residues 21 to 54, we assume this is the site of interaction with D-AKAP2.

Whilst the present invention is founded upon observations made with FMDV 2C, the strong homology between the 2C proteins of all picornavirus, caliciviruses, comoviruses, nepoviruses etc. is recognised in the art and acknowledged in the literature.

The reference to "picornavirus protein 2C" herein refers not only to the 2C protein of picornaviruses alone, but also to the 2C protein of the picornavirus "supergroup" which includes caliciviruses, hepatitis E viruses, comoviruses and nepoviruses.

STATEMENT OF THE INVENTION

Figure 1:
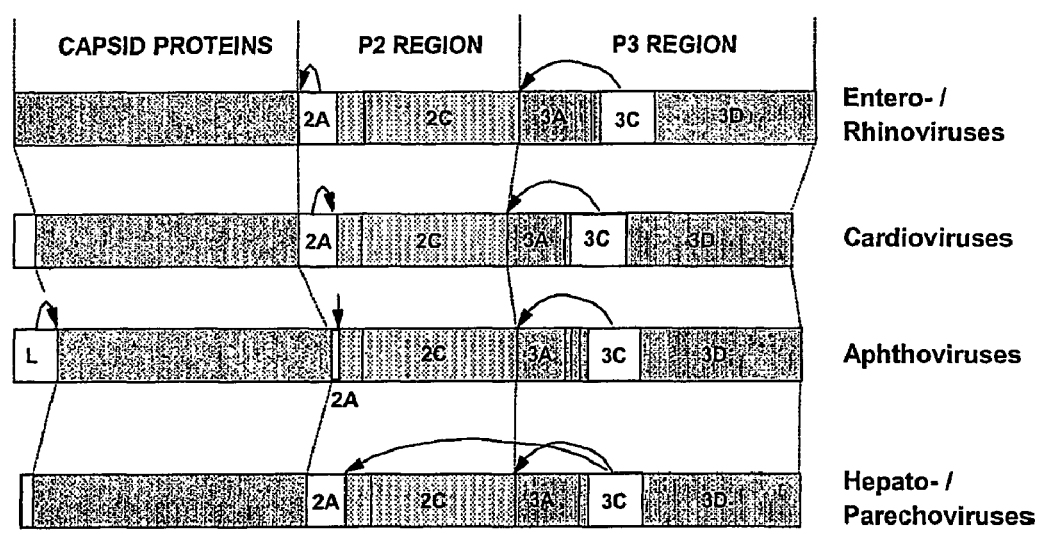
FIG. 1 is a schematic illustration of the polyprotein expressed from the RNA genome of different picornaviruses, and shows the capsid (P1), P2 and P3 regions.
Figure 2:
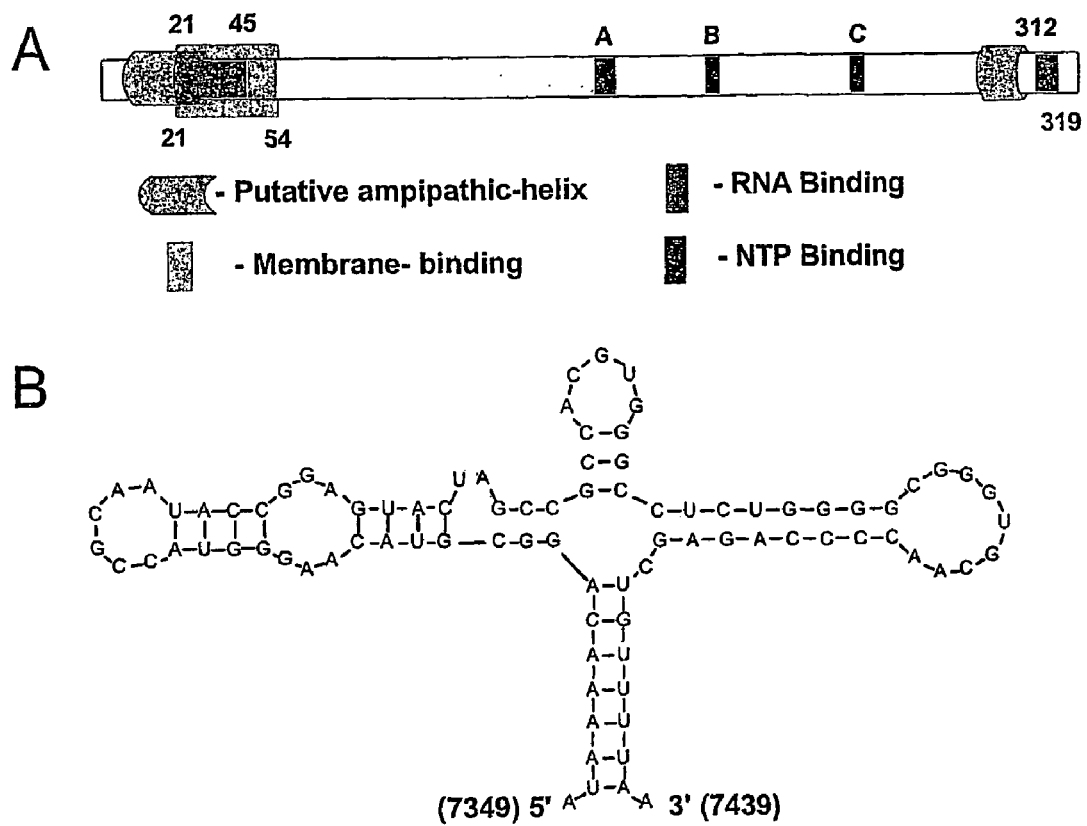
FIG. 2A is a schematic illustration of the domains in protein 2C of poliovirus and shows the putative amphipathic helices, membrane binding, RNA binding and NTP binding domains.
FIG. 2B shows a picornavirus RNA sequence (SEQ ID NO: 7) in a secondary (clover leaf) structure, in which the "stem" forms the binding site for protein 2C.

The present invention provides an assay to select agents which disrupt the interaction of picornavirus protein 2C with D-AKAP2.

Preferably the assay selects agents which bind specifically to the 2C protein or to D-AKAP2. Generally the assay looks for agents which disrupt the 2C:D-AKAP2 association to the extent that replication of the picornavirus is hindered or prevented. Optionally the assay is conducted in an in-vitro system.

The present invention provides an anti-viral agent to combat (ie to prevent or hinder) replication of a picornavirus, said agent disrupting the association between picornavirus protein 2C and D-AKAP2 which occurs during viral replication in a host cell.

The anti-viral agent may be a peptide (for example, a synthetic peptide) or more preferably may be a non-peptidal compound having peptidomimetic properties, ie. is able to mimic a peptide functionally. Such a non-peptidal compound or certain synthetic peptides will be preferred if resistant to enzymic breakdown by peptidases. An example of a synthetic peptide resistant to peptidases includes retro-inverso (RI) peptides, that is peptides formed using the D-isomer of naturally occurring L-amino acids. Suitable anti-viral compounds may include peptides having an amino acid sequence derived from the N-terminal 20 amino acids of 2C, a functional equivalent of such a peptide, or a peptidomimetic compound therefor. The anti-viral agent desirably binds specifically to the 2C protein or to D-AKAP2.

The anti-viral agent is preferably effective against a picornavirus selected from polio, FMDV, enteroviruses, rhinoviruses, hepatitis A viruses, parechoviruses, aphthoviruses, cardioviruses and the like.

In a further aspect, the present invention provides an assay to determine the ability of a test substance to interfere with (preferably to inhibit) the association of picornavirus protein 2C with D-AKAP2, said assay comprising:
    (i) providing a first component consisting of picornavirus protein 2C;
    (ii) providing a second component consisting of D-AKAP2;
    (iii) exposing said first component to a test substance followed by addition of said second component, or exposing said second component to said test substance followed by addition of said first component, or exposing said first component to said second component followed by addition of said test substance;
    (iv) incubating the mixture obtained in step (iii) for a time period and under conditions suitable to allow interaction between the components and/or the test substance;
    (v) removal of any unassociated first or second component and/or test substance;
    (vi) detecting the presence, and optionally determining the amount, of associated first and second components.

The first or second components may be localised on a surface, such as a blotting membrane or an assay plate for ELISA etc.

Detection of the presence and/or amount of second component associated with the first component may be conducted by any convenient means. Generally detection may be via an antibody, for example monoclonal antibody, the presence of which is established by exposure to a second labelled monoclonal antibody in a typical ELISA-style assay. Alternatively, one of the first and second components may be labelled (eg radioactively, fluorescently or enzymically) to determine its binding to the other component.

In a yet further aspect, the present invention provides a method of combating (especially preventing or hindering) replication of a picornavirus, said method comprising providing an anti-viral agent capable of disrupting the association between picornavirus protein 2C and D-AKAP2 which occurs during viral replication in the host cell.

Generally said agent is able to bind specifically to 2C or to D-AKAP2 thereby inhibiting the interaction between these two components which occurs during normal picornavirus replication.

The assay described above can also be used to study cellular biological aspects of the viral infection in cells or to study and elucidate the structure of the D-AKAP2:2C complex. Elucidation of these structures would provide a quantum leap in the understanding of virus replication and provide new potential drug targets.

Optionally the assay may utilise a co-expression construct able to co-express D-AKAP2 together with the virus replication proteins which will self-process and associate from a [P2P3] polyprotein. The construct takes advantage to the fact that the viral proteins are expressed as a self-processing polyprotein. Advantageously D-AKAP2 can be linked to the P2/P3 region via an appropriate 2A proteinase cleavage site. In this manner co-expression of all the components of a replication complex together with D-AKAP2 is achieved.

An example of an assay according to the invention is described hereinbelow:

EXAMPLE (i) Generation of Reagents

We have already cloned and expressed the C-terminal region of porcine D-AKAP2 in *E. coli* as a glutathione S-transferase (GST) fusion protein. We have cloned porcine D-AKAP2 and have access to human D-AKAP2 cDNA. These will be expressed and used to raise (rabbit) monospecific antibodies. We have cloned and expressed FMDV 2C in *E. coli* as a glutathione S-transferase (GST) fusion protein[31]. Differentiating infection from vaccination in foot-and-mouth disease using a panel of recombinant, nonstructural proteins in ELISA. Vaccine 16. 446–459) and used this expressed material to raise (rabbit) antibodies. The titres were low, however, and this work needs to be (partially) repeated to generate higher affinity/titre antibodies. We have also cloned and expressed virus replication proteins 3A, 3B, 3C and 3D[31, 37, 38].

(i) FMDV 2C—*E. coli* Expression

FMDV 2C protein sequences were cloned into the pGEX *E. coli* expression vector (Pharmacia) as described (M. Flint, Thesis).

(ii) FMDV 2C—Transcription In Vitro

Sequences encoding 2C were amplified using the polymerase chain reaction (PCR) from plasmid pMR15[45]. Unique BamHI and EcoRI sites were created at the termini and the doubly restricted, gel purified, PCR product was ligated into the vector pcDNA3.1 (Invitrogen), similarly restricted.

(iii) GST:D-AKAP2 Fusion Protein

The D-AKAP2 specific clone IAP3 (identified by the yeast 2-hybrid screen) was used as the template in the PCR. D-AKAP2 sequences were amplified using oligonucleotide primers;

AKAPF (5'-AAAGGATCCAAAGGGTCCATGTTCTCA-CAAGC-3') SEQ ID NO:1 and

AKAPR (5'-AAAGAATTCTCACAGCTTGGCAGAG-GTCTCC-3') SEQ ID NO: 2.

The PCR product was doubly restricted with BamHI and EcoRI, gel purified, and ligated into the vector pGEX-2T (Pharmacia) similarly restricted. The GST:D-AKAP2 fusion protein (GST-IAP3) was expressed in *E. coli* strain BL21 (DE3). Overnight cultures were grown at 37° C., used to inoculate fresh Luria broth, and the culture grown at 37° C., with vigourous aeration, until the optical density of the culture was 0.6. Isopropyl-1-thio-β-D-galactopyranoside (IPTG) was then added to a final concentration of 1 mM and the culture incubated for a further 1 hr (37° C., aeration). Cells were harvested by centrifugation and the pellets resuspended in ice-cold phosphate buffered saline (PBS). Cells were disrupted by two rounds of sonication (10 s each, cooling on ice between bursts). The mixture was clarified by centrifugation (13,000 g, 2 min, 4° C.) the supernatant then being mixed with a slurry of glutathione sepharose beads for 10 mins at room temperature. The beads were then washed 3 times with PBS prior to use in the 2C binding experiments.

(iv) Mutated Forms of FMDV 2C

Using the overlap PCR technique the NTPase motif "A" of 2C was mutated by a single coding change (Lys116->Gln). PCR Reactions were performed using plasmid pMR15 as the template and oligonucleotide primers.

5'2C
(5'GATATCGGATCCATGCTCAAAGCACGTGACATC-3')
(SEQ ID NO:3)
and

3'2C (Lys116Gln)
(5'-GTTTGCAAGGAAGCTGCCGCCCTGGCCCTGGCCAGATTT-3')
(SEQ ID NO:4)

and a second reaction using primers;

5'2 (Lys116Gln)
(5'-AAATCTGGCCAGGGCGGCAGCTTCCTTGCAAAC-3')
(SEQ ID NO:5)
and 3,2c
(5'GATATCGAATTCTCACTGCTTGAAGATCGGGTG-3')
(SEQ ID NO:6).

The PCR products from each reaction were purified, added, then further amplified using primers 5'2C and 3'2C. The product from this overlap PCR reaction was restricted with BamH1 and EcoR1 and ligated into pGEX-2T, similarly restricted.

(v) FMDV 2C:GST-IAP3 Binding Assay

Transcription vector cDNA clones encoding the wild-type FMDV 2C protein or the mutated form of 2C (Lys116->Gln) were translated in vitro using the TnT Quick rabbit reticulocyte lysate system (Promega), as per the manufacturer's instructions. Proteins were radio-labelled using $^{35}$S-methinone. In vitro translation mixtures were incubated with either GST protein bound to glutathione sepharose beads, or the GST-IAP3 fusion protein bound to glutathione sepharose beads. Typically, 10 μl of translation mixture was incubated with 10 μl of the bead slurry (50% suspension in PBS) with bound GST or GST-IAP3 in 1 ml binding buffer. Binding assays were performed at 4° C. for 30 minutes, the mixture centrifuged to separate the unbound fraction from the beads. Beads were then washed four times in binding buffer prior to analysis by SDS PAGE.

REFERENCES

[1] Ryan, M D. & Flint, M. (1997). J. Gen. Virol. 78, 699–723.

[2] Donnelly, M. L. L., Gani, D., Flint, M., Monaghan, S. & Ryan, M. D. (1997). J. Gen. Virol. 78, 13–21.

[3] Ryan, M. D. & Drew, J. (1994). EMBO J. 134, 928–933.

[4] de Felipe, P., Martín, V., Cortés, M. L., Ryan, M. D. & Izquierdo, M. (1999). Gene Therapy 6, 198–208.

[5] Halpin, C., Cooke, S. E., Barakate, A., El Amrani, A. & Ryan, M. D. (1999). Plant J. 17, 453–459.

[6] Chaplin, P. J., Camon, E. B., Villarreal-Ramos, B., Flint, M., Ryan, M. D. & Collins, R. A. (1999). J. Interferon & Cytokine Res. 19, 235–241.
[7] Dales S., Eggers H. J., Tamm I. & Palade, G. (1965). Virology 26, 379–389.
[8] Bienz, K., Egger, D., Rasser, Y. & Bossart, W. (1983). Virology 131, 39–48.
[9] Irurzun A., Perez L. & Carrasco, L. (1992). Virology 191, 166–175
[10] Maynell L. A. Kirkegaard K. & Klymkowsky, M. W. (1992). J. Virol. 66, 1985–1994.
[11] Barco, A. & Carrasco, L. (1995). EMBO J. 14, 3349–3364.
[12] Doedens J. R. & Kirkegaard, K. (1995). EMBO J. 14, 994–907.
[13] Semler, B. L., Anderson, C. W., Hanecak, R., Dorner, L. F. & Wimmer, E. (1982). Cell 28, 405–412.
[14] Bienz, K., Egger, D., Rasser, Y. & Bossart, W. (1983). Virology 131, 39–48.
[15] Tershak D. R. (1984). J. Virol. 52, 777–783.
[16] Gorbalenya, A. E., Blinov, V. M., Donchenko, A. P. & Koonin, E V. (1989). J. Mol. Evol. 28, 256–268.
[17] Rodriguez, P. L. & Carrasco, L. (1993). J. Biol. Chem. 268, 8105–8110.
[18] Mirzayan, C. & Wimmer, E. (1994). Virology 189, 547–555.
[19] Rodriguez, P. L. & Carrasco, L. (1995). J. Biol. Chem. 270, 10105–10112.
[20] Faux, M C. & Scott, J. D. (1996). Cell 85, 9–12.
[21] Lester, L. B. & Scott, J. D. (1997). Recent Prog. Hormone Res. 52, 409–430.
[22] Colledge, M. & Scott, J. D. (1999). Trends Cell Biol. 9, 216–221.
[23] Sarkar, D., Erlichman, J. & Rubin, C. S. (1984). J. Biol. Chem. 259, 9840–9846.
[24] Lohmann, S. M., Decamilli, P., Einig, I. & Walter, U. (1984). P.N.A.S. USA 81, 6723–6727.
[25] Huang, L. J-S., Durick, K., Weiner, J. A., Chun, J. & Taylor S. S. (1997). P.N.A.S. USA 94, 11184–11189.
[26] Accession No. AF037439; Chatterjee, T. K. & Fisher, R. A. (unpublished)
[27] Knox, C., Miskin, J., Rao, T. V. S., Ryan, M. D. & Wileman, T. (m.s. prepared for publication).
[28] Newlon, M. G., Roy, M., Morikis, D., Hausken, Z. E., Coghlan V., Scott, J. D. & Jennings, P. A. (1999). Nature Struct. Biol. 6, 222–227.
[29] Cowton, V. PhD Thesis, Uni. St. Andrews (Submitted~Supervisor Dr. M. D. Ryan).
[30] Huang, L. J-S., Wang, L., Ma, Y., Durick, K., Perkins, G., Deerinck, T. J., Ellisman, M. H. & Taylor, S. S. (1999). J. Cell Biol., 145, 951–959.
[31] Mackay, D. K. J., Forsyth, M. A., Davies, P. R., Berlinzani, A., Belsham, G. J., Flint, M. & Ryan, M. D. (1998). Vaccine 16, 446–459.
[31a] Flint, M. (1995). Thesis, University of Reading.
[32] Flint, M. (1995). PhD Thesis, Uni. Reading (Supervisor Dr. M. D. Ryan).
[33] Newman, J. F. E., Piatti, P. G., Gorman, B. M., Burrage, T. G., Ryan, M. D., Flint, M. & Brown, F. (1994). Proc. Natl. Acad. Sci. U.S.A. 91, 733–737.
[34] Petersen, J. F., Cherney, M. M., Liebig, H. D., Skern, T., Kuechler, E. & James, M. N. (1999). EMBO J. 18, 5463–5475.
[35] Hansen, J. L., Long, A. M. & Schultz, S. C. (1997). Structure 5, 1109–1122.
[36] O'Reilly, E. K. et al., (1998). Virology 252, 287–303.
[37] Audigier Y., Nigam, S. K., & Blobel, G. (1988) J. Biol. Chem. 263 16352–16357.
[38] Berman, D. M., Wilkie, T. M. & Gilman, A. (1996). Cell 86, 445–452.
[39] Newlon, et al., (1999). Nature Struct. Biol. 6, 222–227.
[40] Denker, et al., (1996). J. Cell. Biol. 133, 1027–1040.
[41] Liu, Z., Donahue, R. E., Young, N. S. & Brown, K. E. (2000). Virology 272, 168–176.
[42] Marvil, P., Knowles, N. J., Mockett, A. P. A., Britton, P., Brown, T. D. K. & Cavanagh, D., (1999). J. Gen. Virol. 80, 653–662.
[43] Ghosh, R. C., Ball, B. V., Willcocks, M. M. & Carter, M. J. (1999). J. Gen. Virol. 80, 1541–1549.
[44] Van der Wilk, F., Dullemans, A. M., Verbeek, M. & Van de Heuvel, J. F. J. M. (1997). Virology 238, 353–362.
[45] Ryan, M. D., Belsham, G. J. & King, A. M. Q. (1989). Specificity of enzyme-substrate interactions in foot-and-mouth disease virus polyprotein processing. Virology 173. 35–45.

The invention claimed is:

1. An assay to determine the ability of a test substance to interfere with the association of protein 2C of a picornavirus or a protein 2C homolog from a calicivirus with dual-specificity kinase anchoring protein 2 (D-AKAP2), said assay comprising:
   i) providing a first component consisting of protein 2C of a picornavirus or a protein 2C homolog from a calicivirus;
   ii) providing a second component consisting of DAKAP2;
   iii) exposing said first component to a test substance followed by addition of said second component, or exposing said second component to said test substance followed by addition of said first component, or exposing said first component to said second component followed by said test substance;
   iv) incubating the mixture obtained in step (iii) for a time period and under conditions suitable to allow interaction between the components and/or the test substance;
   v) removal of any unassociated first or second component and/or test substance; and
   vi) detecting the presence, and optionally determining the amount, of associated first and second components.

2. The assay as claimed in claim 1 which is conducted in vitro.

3. The assay as claimed in claim 1 wherein either the first or second components is localised on a surface.

4. The assay as claimed in claim 1 wherein association of said first and second components is detected by using an antibody, a radio-label, fluorescence, or an enzymic-label.

5. The assay as claimed in claim 1 wherein picornavirus protein 2C and D-AKAP are expressed from a co-expression construct.

6. The assay as claimed in claim 5 wherein said co-expression construct expresses D-AKAP2 and also expresses picornavirus protein 2C, wherein said protein 2C is present as part of a P2/ P3 polyprotein having a 2A proteinase cleavage site, and wherein said DAKAP2 is linked to the P2/ P3 polyprotein via a 2A proteinase cleavage site.

* * * * *

UNITED STATES PATENT AND TRADEMARK OFFICE
CERTIFICATE OF CORRECTION

| | | |
|---|---|---|
| PATENT NO. | : 7,148,022 B2 | Page 1 of 1 |
| APPLICATION NO. | : 10/450342 | |
| DATED | : December 12, 2006 | |
| INVENTOR(S) | : Martin Ryan et al. | |

It is certified that error appears in the above-identified patent and that said Letters Patent is hereby corrected as shown below:

On the Title page, in field (75), Inventors, change "Michael" to --Martin--.

Signed and Sealed this

First Day of May, 2007

JON W. DUDAS
*Director of the United States Patent and Trademark Office*